United States Patent [19]

Kuo

[11] Patent Number: 5,200,520

[45] Date of Patent: Apr. 6, 1993

[54] PROCESS FOR THE PRODUCTION OF PIPERAZINYLPYRIMIDINE DERIVATIVES

[75] Inventor: David L. Kuo, Brig, Switzerland

[73] Assignee: Lonza Ltd., Gampel/Valais, Switzerland

[21] Appl. No.: 804,372

[22] Filed: Dec. 10, 1991

[30] Foreign Application Priority Data

Dec. 18, 1990 [CH] Switzerland ............... 4014/90

[51] Int. Cl.$^5$ ............................... C07D 403/04
[52] U.S. Cl. ................. 544/295; 544/402
[58] Field of Search ....................... 544/295

[56] References Cited

U.S. PATENT DOCUMENTS

| | | | |
|---|---|---|---|
| 4,818,756 | 4/1989 | Seidel et al. | 514/224 |
| 4,937,343 | 6/1990 | Seidel et al. | 544/295 |
| 4,988,809 | 1/1991 | Seidel et al. | 544/121 |

FOREIGN PATENT DOCUMENTS

| | | |
|---|---|---|
| 0129128 | 12/1984 | European Pat. Off. . |
| 0330263 | 8/1989 | European Pat. Off. . |
| 39680 | 4/1976 | Japan . |

OTHER PUBLICATIONS

D. J. Brown et al., The pyrimidines (1962) pp. 31–43.
D. J. Brown et al., The pyrimidines Supplement I (1970) pp. 20–24.
Makin, S. M., et al., Zhurnal Organicheskoi Khimii, (1972), pp. 1415 to 1417.

*Primary Examiner*—Cecilia Tsang
*Attorney, Agent, or Firm*—Fisher, Christen & Sabol

[57] ABSTRACT

A process for the production of piperazinylpyrimidine derivatives of the formula I:

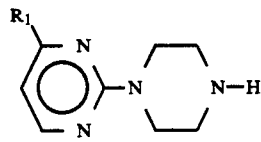

wherein $R_1$ is a hydrogen atom or a $C_1$–$C_4$ alkyl group, branched or unbranched. In the process, piperazine or its hydrate is acid-converted with cyanamide to an amidine salt and the latter is then reacted with a carbonyl compound in the presence of a base to the end product.

19 Claims, No Drawings

PROCESS FOR THE PRODUCTION OF PIPERAZINYLPYRIMIDINE DERIVATIVES

BACKGROUND OF THE INVENTION

1. Field of the Invention

The invention relates to a new process for the production of piperazinylpyrimidine derivatives of the formula:

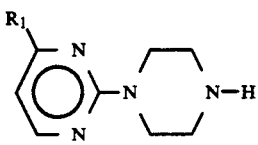
I wherein $R_1$ is a hydrogen atom or a $C_1$–$C_4$ alkyl group, branched or unbranched.

2. Background Art

The piperazinylpyrimidine derivatives of formula I are important intermediate products for the production of pharmaceutical products, such as, for the production of 4-methyl-2-piperazinylpyrimidine, which reduces the blood-sugar level [European Published Patent Appln. No. 0330263].

A process for the production of piperazinylpyrimidine derivatives is described in European Published Patent Application No. 0330263. In the process, a 2-chloropyrimidine is converted with piperazine to a piperazinylpyrimidine derivative. Drawbacks of the process lies in the facts that chloropyrimidines are difficult to obtain and that the end products are obtained in poor yield.

BROAD DESCRIPTION OF THE INVENTION

The main object of the invention is to eliminate above-described drawbacks and to make available a simple and economical process for the production of piperazinylpyrimidine derivatives and wherein the end product can be isolated in a good yield and with a high degree of purity. Other objects and advantages of the invention are set out herein or obvious herefrom to one skilled in the art.

The objects and advantages of the invention are achieved by the process of the invention.

The invention process for the production of piperazinylpyrimidine derivatives of the formula:

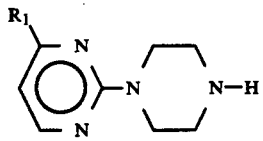
I wherein $R_1$ is a hydrogen atom or a $C_1$–$C_4$ alkyl group, branched or unbranched, is performed so that in the first stage, piperazine of the formula:

II or its hydrate is acid-reacted with cyanamide in a known way, according to Japan Published Patent Application No. 51-39680, to an amidine salt of the formula:

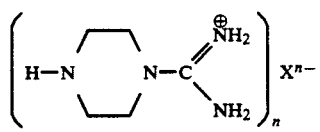
III wherein X is a salt anion and n corresponds to the valence of this salt anion. The amidine salt of formula III is optionally isolated and then, in the second stage, reacted with a carbonyl compound of the formula:

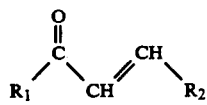
IV wherein $R_1$ is defined above and $R_2$ is a $C_1$–$C_4$ alkoxy group or an amino group, which is substituted or unsubstituted, in the presence of a base to the end product.

DETAILED DESCRIPTION OF THE INVENTION

Suitably, the reaction in the first stage is performed, according to Japan Published Patent Application No. 51-39680, with 1 to 1.5 mol of cyanamide, preferably with 1.1 mol of cyanamide, relative to 1 mol of piperazine or its hydrate. Suitably, the reaction in the first stage is performed at a temperature of 40° to 60° C. Suitably, the reaction in the first stage is performed in the presence of a mineral acid. As a mineral acid, for example, sulfuric acid, hydrochloric acid or phosphoric acid can be used; consequently, $x^{n-}$ in the amidine salt then means chloride, sulfate or phosphate. In particular, concentrated sulfuric acid is used as a mineral acid. Preferably, the mineral acid and the piperazine or its hydrate are used in equimolar amounts for the first stage.

After a usual reaction time of 1 to 2 hours, the amidine salt is then optionally obtained (isolated) according to usual working-up methods, e.g., by concentration by evaporation.

In the second stage, the reaction of the amidine salt with a carbonyl compound takes place with the carbonyl compounds according to the formula:

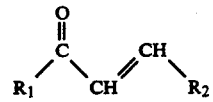
IV wherein $R_1$ has the above meaning and $R_2$ is a $C_1$–$C_4$ alkoxy group or an amino group, which is substituted or unsubstituted. Preferred compounds of formula IV are:

trans-4-methoxy-3-buten-2-one ($R_2$ represents a methoxy group), and

N,N'-dimethylaminoacrolein ($R_2$ represents a dimethylamino group).

The production of N,N'-dimethylaminoacrolein, as a representative of the compounds of formula IV, takes place starting from ethyl vinyl ether with dimethylformamide and $POCl_3$ in dichloroethane [S. M. Makin et al., Zhurnal Organicheskoi Khimii (Journal of Organic Chemistry), (1972), pages 1415 to 1417].

Suitably, the reaction in the second stage is performed with 0.5 to 2 mol of carbonyl compound, preferably with 0.8 to 1 mol, relative to 1 mol of amidine salt, at a suitable temperature of 50° C. up to reflux temperature, preferably at reflux temperature. Suitably, the reaction in the second stage is performed in a polar solvent. As a polar solvent, low-boiling alcohols, such as, methanol or ethanol, can be used. Dimethyl sulfoxide or dimethylformamide can also be suitable as the solvent. Preferably, methanol is used as the solvent. The reaction in the second stage with the carbonyl compound is performed in the presence of a base. As a base, an alcoholate can be used, such as, sodium methylate or sodium ethylate. Preferably, sodium methylate is used. Preferably, the base is used in an amount of 2 to 5 mol, relative to 1 mol of the carbonyl compounds.

After a usual reaction time of 3 to 8 hours, the end product is then isolated according to usual working-up methods, such as, by extraction and distillation.

Preferably, 2-(1-piperazinyl)pyrimidine and 4-methyl-2-(1-piperazinyl)pyrimidine are obtained as the end products.

EXAMPLE 1

Production of N,N'-dimethylaminoacrolein (Not According to the Invention)

At 0° C., a solution of 30.6 g of $POCl_3$ (0.2 mol) in dichloroethane (30 ml) was added by instillation to a solution of 29.2 g of dimethylformamide (0.4 mol) in dichloroethane (60 ml).

Then, a solution of ethyl vinyl ether (14.4 g, 0.2 mol) in dichloroethane (20 ml) was added. The reaction mixture was heated for 3 hours to 70° C., then cooled to 0° C. and then $H_2O$ (80 ml) was added—all of this material was stirred overnight. At 0° C., a saturated $K_2CO_3$ solution (200 ml) was added by instillation, then was extracted with $CHCl_3$ five times (50 ml each), and the combined organic phases were washed once with $H_2O$ (100 ml) and dried on $Na_2SO_4$. After distilling off the solvent in a vacuum, 38.1 g of a bright orange-red liquid was obtained, which, after further distillation (0.8 mbar, 100° C.), yielded 11.9 g of N,N'-dimethylaminoacrolein, as a yellow liquid, corresponding to a yield of 60.3 percent.

EXAMPLE 2

Production of 2-(1-piperazinyl)-amidino Sulfate (Not According to the Invention)

95.6 percent sulfuric acid (74.5 g, 0.72 mol) was added to piperazinehexahydrate (552 g, 2.78 mol) within 10 minutes. This mixture was heated to 50° C. and then a 25 percent aqueous solution of cyanamide (484 g, 2.88 mol) was slowly added within 2 hours. After further stirring for 2 hours at 50° C., 95.6 percent sulfuric acid (0.47 mol) was added within 10 minutes which led to a temperature increase to about 63° C. Then, the mixture was evaporated to dryness and absolute methanol (800 ml) was added to this sticky mass (601 g) and cooled for 1 hour. Then, the solution was filtered and washed with cold absolute methanol twice (100 ml). After drying in a vacuum, 328 g of 2-(1-piperazinyl)-amidino sulfate, corresponding to a yield of 77.3 percent, was obtained. The mother liquor was cooled for 2 days, then filtered, washed twice with absolute methanol (50 ml) and dried under a vacuum. 43.3 q of 2-(1-piperazinyl)-amidino sulfate, corresponding to a yield of 10.2 percent, was obtained. After combining these two fractions, the total yield was 87.6 percent, relative to the initial product.

EXAMPLE 3

Process for the Production of 2-(1-piperazinyl)pyrimidine

Absolute methanol (100 ml) and then sodium methylate, 30 percent in methanol, (52.9 0.29 mol) were added to 2-(1-piperazinyl)- amidino sulfate (50 g, 0.14 mol). The mixture was refluxed and then N,N'-dimethylaminoacrolein (12.3 g, 0.118 mol) was slowly added within 1.5 hours. Then, the mixture was stirred for 4 hours under reflux, cooled to room temperature, cold $H_2O$ (300 ml) was added, and the mixture was filtered. The filtrate was extracted 4 times with $CHCl_3$ (100 ml) and the combined organic phases were dried on $Na_2SO_4$. After removal of the solvent in a vacuum, 21.4 g of the product was obtained, and after distillation (0.45 mbar, 98 to 100° C.), then 16.1 g of the product corresponding to a yield of 83 percent, relative to the amidino sulfate, with a content of more than 96 percent (GC), was obtained.

EXAMPLE 4

Production of 4-methyl-2-(1-piperazinyl)pyrimidine

Sodium methanolate (24.2 ml, 128 mmol) was added to a solution of 2-(1-piperazinyl)-amidino sulfate (13.6 g, 38.5 mmol) in absolute methanol (20 ml). The mixture was refluxed for 10 minutes to 80° C. Then, trans-4-methoxy-3-buten-2-one (5.14 g, 51.3 mmol) dissolved in absolute methanol (20 ml) was added within 2.5 hours. After completion of the reaction, the mixture was stirred for 2 more hours at 80° C. After the cooling, it was extracted 5 times with $CHCl_3$ (20 ml), the combined organic phases were washed once with $H_2O$ (20 ml), dried on $Na_2SO_4$. After removal of the solvent in a vacuum, 6.14 g of light brown residue was obtained. After distillation (130° to 150° C., 0.5 mbar), 4.93 g of 4-methyl-2-(1-piperazinyl) pyrimidine, corresponding to a yield of 53.9 percent, relative to the amidino sulfate used, was obtained as a colorless oil.

What is claimed is:

1. Process for the production of a piperazinylpyrimidine compound of the formula:

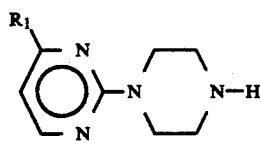

I wherein $R_1$ is a hydrogen atom or a $C_1$–$C_4$ alkyl group, branched or unbranched, characterized in that, in a first stage, piperazine of the formula:

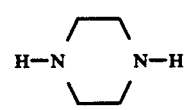

II or its hydrate is acid-related with cyanamide to an amidine salt of the formula:

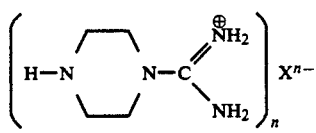

wherein X is an anion which forms said amidine salt and n corresponds to the valence of said anion which forms said amidine salt of formula III is optionally isolated, and then, in a second stage, the amidine salt of formula III is reacted with a carbonyl compound of the formula:

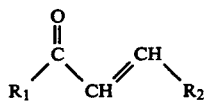

wherein $R_1$ has the above meaning and $R_2$ is a $C_1$–$C_4$ alkoxy group or —$NH_2$, which is substituted or unsubstituted, in the presence of a base to said piperazinylpyrimidine of formula I.

2. Process according to claim 1 wherein the reaction in the first stage is performed with 1 to 1.5 mol of cyanamide, relative to 1 mol of piperazine or its hydrate.

3. Process according to claim 2 wherein the reaction in the first stage is performed in the presence of a mineral acid.

4. Process according to claim 3 wherein the reaction in the first stage is performed at a temperature of 40° to 60° C.

5. Process according to claim 1 wherein trans-4-methoxy-3-buten-2-one is used as the carbonyl compound in the second stage.

6. Process according to claim 5 wherein N,N'-dimethylaminoacrolein is used as the carbonyl compound in the second stage.

7. Process according to claim 6 wherein the reaction in the second stage is performed in a polar solvent.

8. Process according to claim 7 wherein the reaction in the second stage is performed at a temperature of 50° C. to reflux temperature.

9. Process according to claim 8 wherein the reaction in the second stage is performed in the presence of an alcoholate as a base.

10. Process according to claim 1 wherein the reaction in the first stage is performed in the presence of a mineral acid.

11. Process according to claim 1 wherein the reaction in the first stage is performed at a temperature of 40° to 60° C.

12. Process according to claim 1 wherein the reaction in the second stage is performed in a polar solvent.

13. Process according to claim 1 wherein the reaction in the second stage is performed at a temperature of 50° C. to reflux temperature.

14. Process according to claim 1 wherein the reaction in the second stage is performed in the presence of an alcoholate as a base.

15. Process according to claim 1 wherein $X^{n-}$ is chloride, sulfate or phosphate.

16. Process according to claim 1 wherein $R_2$ is $NH_2$.

17. Process according to claim 1 wherein $R_2$ is a $C_1$–$C_4$ alkoxy group.

18. Process according to claim 1 wherein $R_1$ is a hydrogen atom.

19. Process according to claim 1 wherein $R_1$ is a $C_1$–$C_4$ alkyl group.

* * * * *